United States Patent
Flagle et al.

(10) Patent No.: US 7,544,205 B2
(45) Date of Patent: Jun. 9, 2009

(54) INTRALUMINAL SUPPORT FRAME AND MEDICAL DEVICES INCLUDING THE SUPPORT FRAME

(75) Inventors: Jacob Flagle, Bloomington, IN (US); Brain C. Case, Bloomington, IN (US)

(73) Assignee: Cook Incorporated, Bloomington, IN (US)

(*) Notice: Subject to any disclaimer, the term of this patent is extended or adjusted under 35 U.S.C. 154(b) by 185 days.

(21) Appl. No.: 11/314,661

(22) Filed: Dec. 20, 2005

(65) Prior Publication Data

US 2006/0173532 A1 Aug. 3, 2006

Related U.S. Application Data

(60) Provisional application No. 60/593,195, filed on Dec. 20, 2004.

(51) Int. Cl.
*A61F 2/06* (2006.01)
(52) U.S. Cl. ............................ 623/1.24; 623/1.15
(58) Field of Classification Search ............ 623/1.15, 623/1.24, 1.25; *A61F 2/06*
See application file for complete search history.

(56) References Cited

U.S. PATENT DOCUMENTS

| | | | |
|---|---|---|---|
| 4,580,568 A | 4/1986 | Gianturco | |
| 5,411,552 A | 5/1995 | Andersen et al. | |
| 6,482,228 B1 | 11/2002 | Norred | |
| 6,494,909 B2 | 12/2002 | Greenhalgh | |
| 6,786,922 B2 | 9/2004 | Schaeffer | |
| 2002/0138131 A1 | 9/2002 | Solovay et al. | |
| 2003/0176914 A1* | 9/2003 | Rabkin et al. | 623/1.15 |
| 2003/0225449 A1* | 12/2003 | Denison | 623/1.15 |
| 2003/0236568 A1 | 12/2003 | Hojeibane et al. | |
| 2004/0019374 A1 | 1/2004 | Hojeibane et al. | |
| 2004/0093070 A1 | 5/2004 | Hojeibane et al. | |
| 2004/0210306 A1 | 10/2004 | Quijano et al. | |
| 2004/0225348 A1 | 11/2004 | Case et al. | |
| 2004/0225356 A1 | 11/2004 | Frater | |
| 2004/0243216 A1* | 12/2004 | Gregorich | 623/1.15 |
| 2005/0004659 A1* | 1/2005 | Von Oepen et al. | 623/1.16 |
| 2005/0060024 A1* | 3/2005 | Lee et al. | 623/1.16 |
| 2005/0065614 A1 | 3/2005 | Stinson | |
| 2005/0096735 A1* | 5/2005 | Hojeibane et al. | 623/1.24 |
| 2006/0282157 A1 | 12/2006 | Hill et al. | |

FOREIGN PATENT DOCUMENTS

| | | |
|---|---|---|
| EP | 1579886 A1 | 9/2005 |
| FR | 2785174 A | 3/1998 |
| WO | WO 0174273 A | 10/2001 |
| WO | WO 2004045703 A1 | 6/2004 |
| WO | WO 2005011535 A2 | 2/2005 |

* cited by examiner

*Primary Examiner*—Corrine M McDermott
*Assistant Examiner*—Jason-Dennis Stewart
(74) *Attorney, Agent, or Firm*—Buchanan Intellectual Property Office LLC

(57) ABSTRACT

Intraluminal support frames for placement within a body vessel are provided. The support frames include a plurality of ring structures and first and second sets of connector segments. Connector segments of the first set join adjacent pairs of ring structures while connector segments of the second set join at least three ring structures. Medical devices are also provided that include a support frame and an additional component, such as a graft member or valve member.

14 Claims, 3 Drawing Sheets

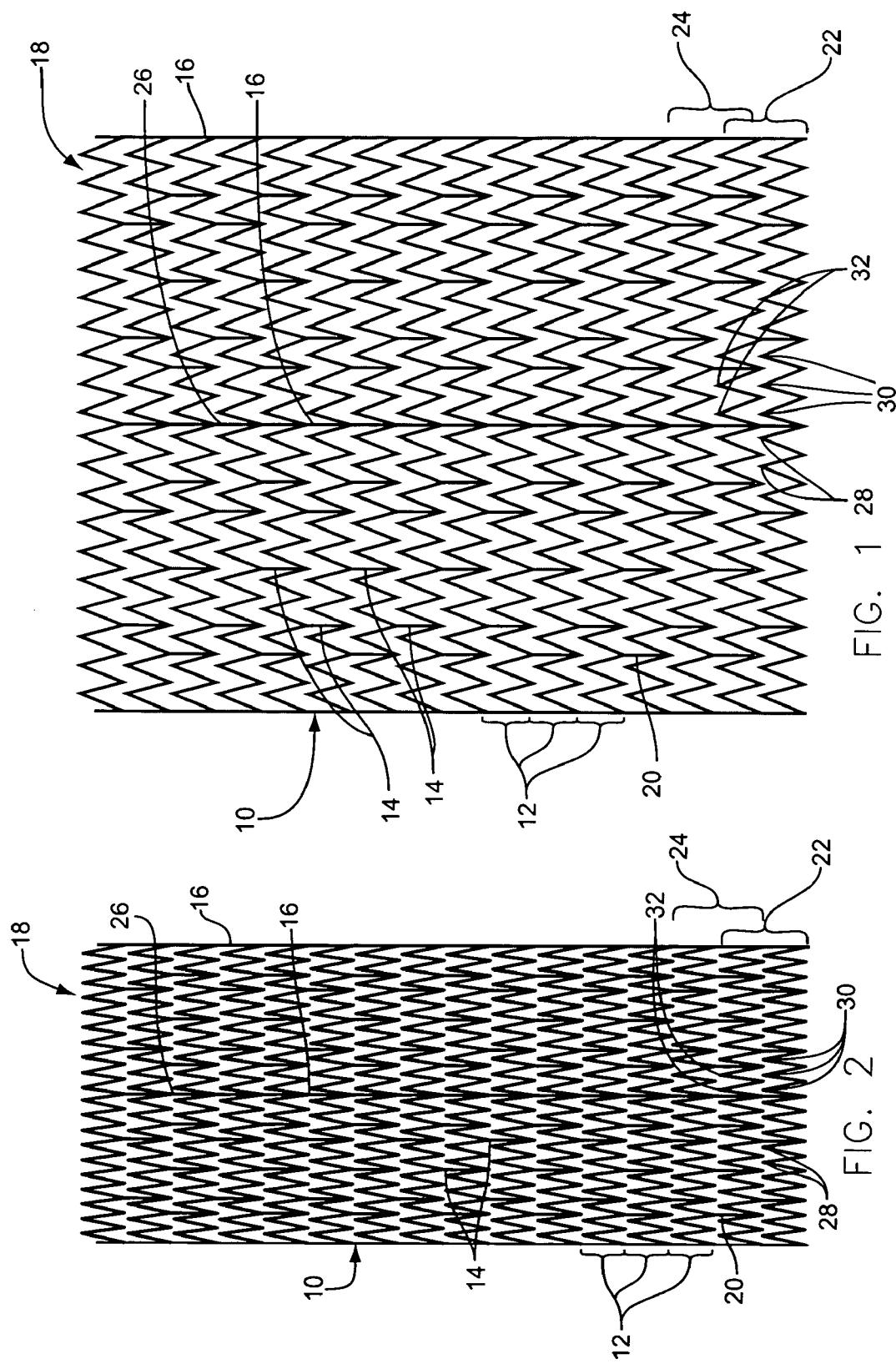

INTRALUMINAL SUPPORT FRAME AND MEDICAL DEVICES INCLUDING THE SUPPORT FRAME

CROSS REFERENCE TO RELATED APPLICATIONS

The present patent application claims priority to the provisional patent application identified by U.S. Ser. No. 60/593,195, filed on Dec. 20, 2004, the entire content of which is hereby expressly incorporated herein by reference.

FIELD

The invention relates generally to the field of medical devices. More particularly, the invention relates to intraluminal support frames and intraluminal medical devices that include an intraluminal support frame.

BACKGROUND

Various types of disease conditions present clinical situations in which a vessel of a patient needs to be artificially supported to maintain an open passageway through which fluids, such as blood, can flow. For example, blood flow through an artery can be impeded due to a build-up of cholesterol on the interior wall of the vessel. Also, vessel walls can be weakened by a variety of conditions, such of aneurysms.

Intraluminal support frames provide an artificial mechanism to support a body vessel. The prior art provides many examples of intraluminal support frames, including an array of cardiovascular stents. Many prior art support frames are tubular-shaped members that are placed in the lumen of the vessel and, once deployed, exert a radially-outward directed force onto the vessel wall to provide the desired support. Support frames can also provide a base architecture onto which additional functionality can be built. For example, graft members and valve members can be attached to a support frame to provide graft and valve devices, respectively. The support frame in these types of devices can serve simply to provide the base architecture, or to both provide the base architecture and a vessel support mechanism as described above.

Intraluminal support frames are typically positioned at a point of treatment in a body vessel by navigation through the vessel, and possibly other connected vessels, until the point of treatment is reached. This navigation requires that the support frame be able to move axially through the vessel(s) while still maintaining the ability to exert an outward force on the interior wall once deployed. Accordingly, intraluminal support frames typically have radially unexpanded and expanded configurations. In the unexpanded configuration, the support frame has a relatively small diameter that allows it to be moved axially through the vessel. In the expanded configuration, the support frame has a relatively large diameter that allows it to engage an interior wall of the body vessel and exert a radially outward directed force on the interior wall, thereby providing the desired support to the vessel.

Once the support frame is navigated to a desired point of treatment in a body vessel, the support frame is deployed by allowing it to assume its expanded diameter. During expansion from the radially unexpanded configuration to the radially expanded configuration, intraluminal support frames can exhibit a degree of foreshortening, which can affect the accuracy of placement of the support frame. Indeed, the foreshortening effect is frequently referred to as a "jumping" of the support frame during deployment. Foreshortening is particularly evident in self-expandable support frames, which do not require an application of force to achieve the expanded configuration. Foreshortening of support frames in a medical device that includes an additional component or components, such as a graft member or a valve member, could have an effect on the functioning of the component(s).

SUMMARY OF EXEMPLARY EMOBODIMENTS

Intraluminal support frames and medical devices that include an intraluminal support frame are described. Support frames according to the invention have a ring architecture and at least one connector strut that connects three or more rings to each other.

An intraluminal support frame according to one exemplary embodiment comprises a plurality of ring structures and first and second sets of connector segments. Each of the first set of connector segments joins an adjacent pair of the plurality of ring structures, and each of the second set of connector segments joins at least three ring structures of the plurality of ring structures.

Medical devices that include a support frame are also described. A medical device according to one exemplary embodiment comprises a support frame according to the invention and an attached graft member.

A medical device according to another exemplary embodiment comprises a prosthetic valve for regulating the flow of fluid through a body vessel. In this embodiment, the medical device comprises a support frame and an attached valve member.

Additional understanding of the invention can be gained by reference to the attached drawings and the detailed description presented below, each of which relate to exemplary embodiments.

BRIEF DESCRIPTION OF THE DRAWINGS

FIG. 1 is a flat pattern view of an intraluminal support frame according to a first exemplary embodiment shown in an expanded configuration.

FIG. 2 is a flat pattern view of the support frame illustrated in FIG. 1 shown in an unexpanded configuration.

DETAILED DESCRIPTION OF EXEMPLARY EMBODIMENTS

Figure 3:
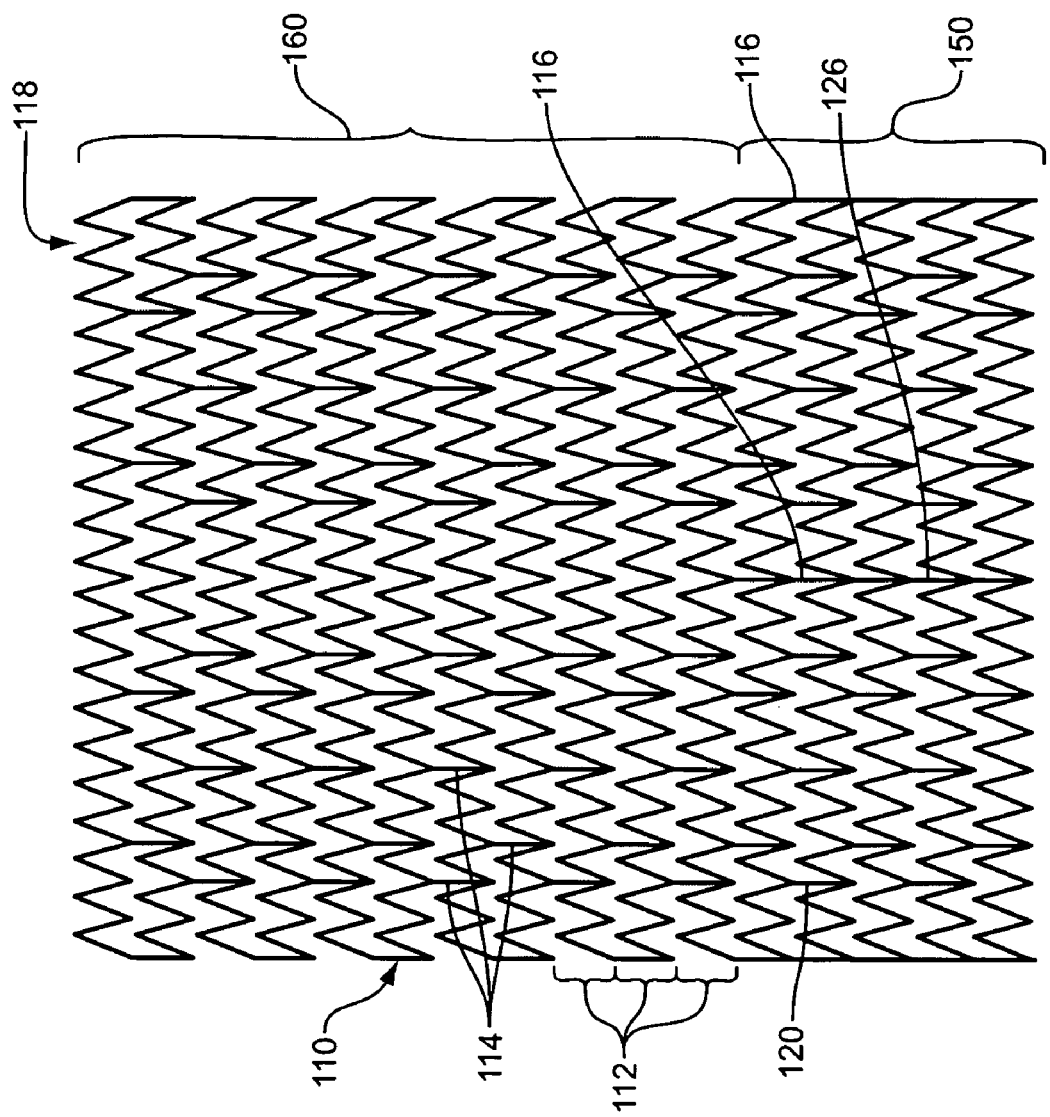
FIG. 3 is a flat pattern view of an intraluminal support frame according to a second exemplary embodiment shown in an expanded configuration.

The following description of exemplary embodiments provides illustrative examples of the invention. The embodiments discussed herein are merely exemplary in nature and are not intended to limit the scope of the invention, or its protection, in any manner. Rather, the description of these exemplary embodiments serves to enable a person of ordinary skill in the relevant art to practice the invention.

FIGS. 1 and 2 illustrate an intraluminal support frame 10 according to a first exemplary embodiment of the invention. Each of FIGS. 1 and 2 are flat pattern views of the support frame 10. Thus, in use, the flat pattern illustrated in the figures is circularized along a lengthwise axis to form a cylindrical support frame that defines an interior passageway. The flat pattern views are presented simply to facilitate understanding of the architecture of the support frame. It is expressly understood that support frames in accordance with the invention do not need to be fabricated by circularizing a flat piece to form a cylindrical member. While this certainly is an acceptable method of fabrication for support frames according to the invention, any suitable method can be used. For example, an appropriate pattern can be cut from a tubular member to form a desirable pattern.

The support frame 10 comprises a plurality of ring structures 12 interconnected by first 14 and second 16 sets of connector segments.

Each ring structure 12 is a substantially circular ring comprising an endless undulating pattern. In the illustrated embodiment, the undulating pattern comprises a serpentine pattern 18. Any suitable ring structure with the desired undulating pattern can be used, including rings formed by bending a wire in a zig-zag pattern and joining the ends. Alternatively, a ring structure can be formed by cutting a suitable pattern from a solid tube of material. Examples of suitable ring structures are described in U.S. Pat. No. 4,580,568 to Gianturco for PERCUTANEOUS ENDOVASCULAR STENT AND METHOD FOR INSERTION THEREOF and U.S. Pat. No. 6,786,922 to Schaeffer for STENT WITH RING ARCHITECTURE AND AXIALLY DISPLACED CONNECTOR SEGMENTS, each of which is hereby incorporated in its entirety into this disclosure for the purpose of describing suitable ring structures for use with the invention.

The support frame 10 can include any suitable number of ring structures 12. The specific number of ring structures 12 included in a particular support frame according to the invention will depend on several factors, including the anticipated axial length of a treatment site at which the support frame may be deployed. The support frame illustrated in FIGS. 1 and 2 includes sixteen ring structures. As a minimum, and based on the interrelationship between the sets 14, 16 of connector segments and the ring structures 12, a support frame according to the invention includes at least three ring structures.

The first set 14 of connector segments join adjacent ring structures 12. As best illustrated in FIG. 1, an individual connector segment 20 of this set 14 extends between two adjacent ring structures 12. The connector segment 20 is advantageously terminated at each of the adjacent ring structures 12 to enhance the overall flexibility of the support frame 10.

The first set 14 of connector segments can include any suitable number of individual connector segments 20. The specific number chosen for any particular support frame according to the invention will depend on several factors, including the desired flexibility of the support frame. Also, as best illustrated in FIG. 1, first 22 and second 24 adjacent pairs of ring structures 12 can have different numbers of first set 14 connector segments interconnecting the respective pairs of ring structures 12. In the illustrated embodiment, four (4) first set 14 connector segments interconnect the ring structures 12 of the first pair 22 while six (6) first set 14 connector segments interconnect the ring structures 12 of the second pair 24. This arrangement is considered advantageous at least because it allows for localized flexibility along the length of the support frame 10.

Also, as best illustrated in FIG. 1, the first set 14 connector segments joining the first pair 22 of ring structures 12 are advantageously disposed out of phase with the first set 14 connector segments joining the adjacent second pair 24 of ring structures 12. This arrangement enhances the overall stability of the support frame 10. As used herein with reference to connector segments, the term "out of phase" describes a spatial relationship between connector segments in which the connector segments lie on different lengthwise axes.

The second set 16 of connector segments join three or more adjacent ring structures 12. In the embodiment illustrated in FIGS. 1 and 2, individual connector segments 26 of the second set 16 of connector segments join all of the ring structures 12 in the support frame 10. The individual connector segments 26 of the second set 16 provide longitudinal stability to the support frame 10 and provide desirable foreshortening characteristics for the support frame 10.

The second set 16 of connector segments can include any suitable number of individual connector segments 26. The specific number chosen for any particular support frame according to the invention will depend on several factors, including the desired longitudinal stability and flexibility of the support frame. In the embodiment illustrated in FIGS. 1 and 2, the second set 16 includes two individual connector segments 26 (note that, as a feature of the flat pattern nature of the drawings, one of the connector segments is split lengthwise). No matter the number chosen, the individual connector segments 26 of the second set 16 can be relatively positioned in any suitable manner. In the embodiment illustrated in FIGS. 1 and 2, the individual connector segments 26 of the second set 16 are diametrically opposed from each other in the cylindrical form of the support frame 10. Other relative positioning of the individual connector segments 26 can be used, including localization of multiple connector segments 26 on one side of the support frame 10. It is also noted that the second set 16 of connector segments can comprise a single individual connector segment 26.

In the embodiment illustrated in FIGS. 1 and 2, at least two peaks 28 of the undulating pattern 18 of a ring structure 12 are disposed between an individual connector segment 26 of the second set 16 of connector segments and each individual connector segment 20 of the first set 14 of connector segments. More or fewer separating peaks 28 can be employed, but a minimum of two is considered advantageous. Also, different pairs of adjacent ring structures 12 can have different numbers of separating peaks. For example, in the embodiment illustrated in FIGS. 1 and 2, three separating peaks 30 are disposed between the first set 14 and second set 16 connector segments that join a first pair 22 of adjacent ring structures 12, while two separating peaks 32 are disposed between the first set 14 and second set 16 connector segments that join a second pair 24 of adjacent ring structures 12.

The support frame 10 is an expandable support frame having radially unexpanded and radially expanded configurations. As such, the support frame 10 can be a self-expandable support frame, such as one fabricated from a shape memory material such as nickel-titanium alloy, a balloon expandable support frame or any other type of expandable frame. FIG. 1 illustrates the support frame 10 in its radially expanded configuration and FIG. 2 illustrates the support frame 10 in its radially unexpanded configuration.

The support frame 10 can be fabricated from any suitable material. The material chosen for any particular support frame according to the invention need only be biocompatible or able to be made biocompatible. Examples of suitable materials include shape memory alloys, such as nickel-titanium alloys, and stainless steel. The ring members 12 and sets 14, 16 of connector segments can be fabricated from the same or different materials using conventional techniques, including winding and braiding techniques as well as laser-cutting techniques.

FIG. 3 illustrates a support frame 110 according to a second exemplary embodiment. FIG. 3 is a flat pattern view of the support frame 110 and illustrates the support frame 110 in a radially expanded configuration.

The support frame 110 according this embodiment is similar to the support frame 10 illustrated in FIGS. 1 and 2, except as described below. Accordingly, similar features and/or components are labeled with similar reference numbers as those in FIGS. 1 and 2, increased by one hundred.

The support frame 110 comprises a plurality of ring structures 112 interconnected by first 114 and second 116 sets of connector segments. Each ring structure 112 has an endless undulating pattern 118. Individual connector segments 120 of the first set of connector segments 114 join a pair of adjacent ring structures 112. Individual connector segments 126 of the second set of connector segments 116 join three or more adjacent ring structures 112.

In this embodiment, each of the individual connector segments 126 of the second set 116 of connector segments joins fewer than all of the ring structures 112 that form the support frame 110. Advantageously, each of the individual connector segments 126 of the second set 116 of connector segments can join less than one half of the ring structures 112 that form the support frame 110. Alternatively, each of the individual connector segments 126 of the second set 116 of connector segments can join fewer than one third of the ring structures 112 that form the support frame, or any other suitable number of ring structures 112 that is less than the total number of ring structures 112 in the support frame 110.

This arrangement of the second set 116 of connector segments forms first 150 and second 160 regions on the support frame 110. The first region 150 includes connector segments from both sets 114, 116, and the second region 160 includes only connector segments from the first set 114. As a result, the first region 150 has enhanced longitudinal stability compared to the second region 160, and exhibits enhanced foreshortening characteristics over those of the second region 160. This differential architecture may be desirable in a variety of applications, including medical devices with functional members, such as graft members and/or valve members, attached to a support frame. An example of such a medical device is described below. Also, this arrangement can be advantageous in applications in which a localization of foreshortening is desired along a portion of the length of a medical device.

Figure 4:
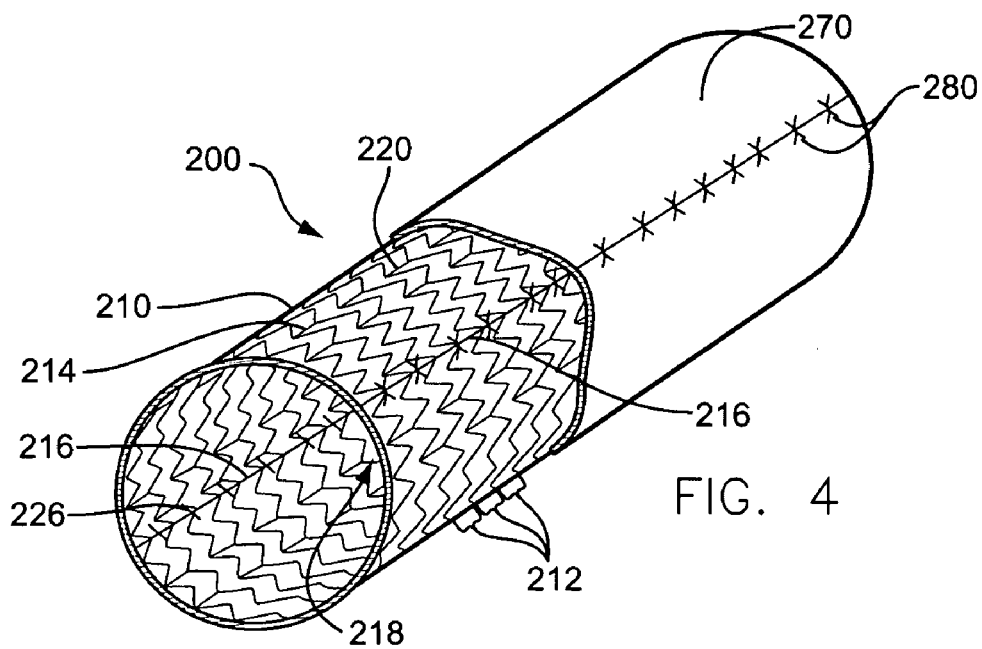
FIG. 4 is a perspective view of a medical device according to a third exemplary embodiment.

FIG. 4 illustrates a medical device 200 according to an exemplary embodiment. The medical device 200 includes a support frame 210 according to the invention and an attached graft member 270.

In the illustrated embodiment, the support frame 210 is the support frame 10 illustrated in FIGS. 1 and 2. Accordingly, similar features and/or components are labeled with similar reference numbers as those in FIGS. 1 and 2, increased by two hundred.

The support frame 210 comprises a plurality of ring structures 212 interconnected by first 214 and second 216 sets of connector segments. Each ring structure 212 has an endless undulating pattern 218. Individual connector segments 220 of the first set 214 of connector segments join a pair of adjacent ring structures 212. Individual connector segments 226 of the second set 216 of connector segments join all ring structures 212 of the support frame 210.

While the illustrated example includes a specific support frame 210 according to the invention, it is understood that the medical device 200 can include any support frame according to the invention.

The graft member 270 is attached to the support frame 210 and is disposed around the support frame 210 and along its entire length. It is understood that the graft member 270 can be disposed around any suitable portion of the support frame 210 and along any suitable length of the support frame 210. Also, the graft member 270 can be disposed on the exterior, the interior, or both the exterior and interior of the support frame 210.

The graft member 270 can be formed of any suitable material, and need only be biocompatible or be able to be made biocompatible. The medical device arts include several examples of suitable materials for use as or in the graft member. The specific material chosen for the graft member in a particular medical device according to the invention will depend on several factors, including the anticipated point of treatment and/or vessel type at which the medical device will be used. Examples of suitable materials include expanded polytetrafluoroethylene (ePTFF), polyurethane, and bioremodellable materials such as, extracellular matrix (ECM) materials, including small intestine submucosa (SIS) and other ECM's. Other bioremodellable materials can be used as well. Tissues and other natural materials can also be used, including processed versions of natural materials, including fixed tissue.

Figure 5:
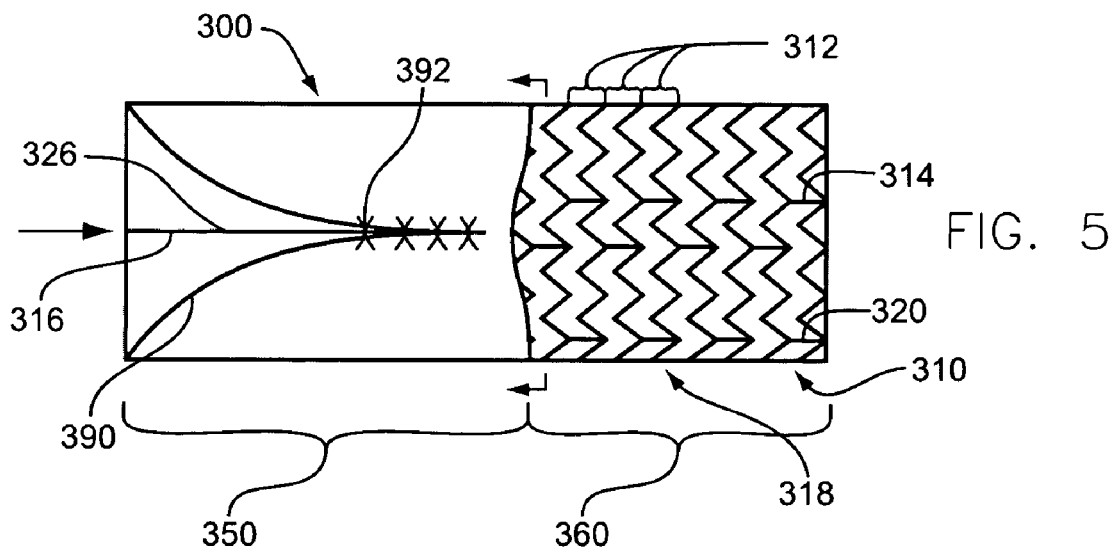
FIG. 5 is an elevational view of a medical device according to a fourth exemplary embodiment.

The graft member 270 is attached to the support frame 210 by attachment elements 280. Any suitable type and number of attachment elements 280 can be used, including sutures, staples, clips, adhesives, and the like. As illustrated in FIG. 5, the graft member 270 is advantageously attached to the support frame 210 at one or more points along the individual connector segments 226 of the second set 216 of connector segments 216. It is expressly understood, though, that the attachment elements 280 can be positioned at any point on the medical device 200 and support frame 210.

The medical device 200 is useful as a supported graft, such as a stent graft, and can be used in a variety of applications, including vessel repair and aneurysm exclusion.

Figure 6:
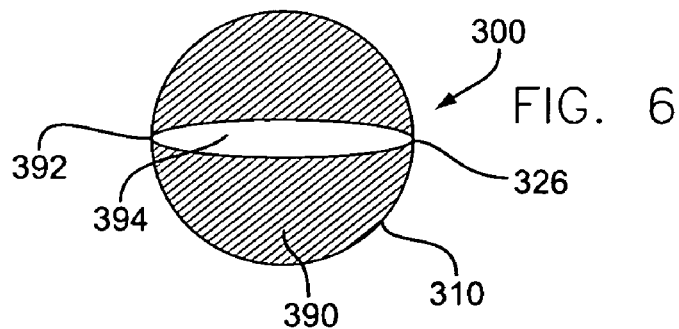
FIG. 6 is an end view of the medical device illustrated in FIG. 5.

FIGS. 5 and 6 illustrate a medical device 300 according to an exemplary embodiment. The medical device 300 according to this embodiment is a prosthetic valve that can be used to regulate fluid flow through a body vessel. The medical device 300 can be used in a blood vessel, such as a vein, or in any other suitable body vessel. Also, the medical device 300 can be used in and/or with a body organ, such as a heart, to provide a valve for the organ and/or augment, replace, or otherwise treat a natural valve associated with the organ. The medical device 300 includes a support frame 310 according to the invention and an attached valve member 390.

In the illustrated embodiment, the support frame 310 comprises a plurality of ring structures 312 interconnected by first 314 and second 316 sets of connector segments. Each of the ring structures 312 has an endless undulating pattern 318. Individual connector segments 320 of the first set 314 of connector segments join an adjacent pair of ring structures 312, while individual connector segments 326 of the second set of connector segments 316 join three or more adjacent ring structures 312. The support frame 310 includes first 350 and second 360 regions, similar to the support frame illustrated in FIGS. 3 and 4. The first region 350 includes connector segments from both the first 314 and second sets 316 of connector segments, while the second region 360 includes only connector segments from the first set 314 of connector segments.

The valve member 390 is attached to the support frame 310 at the first region and advantageously along a portion of the length of one or more connector segments 326 of the second set 316 of connector segments. Attachment elements 392 are used to connect the graft member 390 to the support frame 310. Any suitable type and number of attachment elements, including sutures, staples, clips, adhesives and the like, can be used.

As best illustrated in FIG. 7, the valve member 390 is attached to the support frame 310 in a manner that allows the valve member 390 to form a valve opening 394 that alternately opens and closes to allow and substantially prevent, respectively, fluid flow through the medical device 300.

The valve member 390 can comprise a single member, such as a tubular member, or multiple members, such as multiple valve leaflets. The valve member 290 need only be attached to the support frame in a manner that forms the desired valve opening 394.

Any suitable material can be used for the valve member 390, including natural and synthetic materials. The specific material chosen for a particular medical device according to the invention will depend on several factors, including the intended point of treatment and vessel type at which the medical device will be used and the intended function of the medical device. Examples of suitable materials include polymeric materials, such as polyurethane, and bioremodellable materials, such as SIS and other ECM's. ECM's are considered particularly advantageous at least because of their ability to be tolerated in a variety of in vivo environments and their ability to remodel into natural host tissue. Other currently contemplated materials include bovine pericardium and other natural materials. Tissue valves, which comprise preexisting natural valves harvested from animal tissue, such as a heart or other valve-containing or defining tissue, can be used, as can other suitable tissues or sections thereof. Porcine heart valves are considered particularly well-suited tissue valves for use in medical devices according to the invention. Tissues and other natural materials can be used in their natural state or in a processed form, such as a form rendered substantially biologically inert by chemical treatment. For example, a cross-linked ECM, such as cross-linked SIS, can be used.

The foregoing detailed description provides exemplary embodiments of the invention and includes the best mode for practicing the invention. The description and illustration of embodiments is intended only to provide examples of the invention, and not to limit the scope of the invention, or its protection, in any manner.

We claim:

1. A medical device for regulating fluid flow through a body vessel, said medical device comprising:
   an intraluminal support frame having proximal and distal ends and comprising first and second axial portions and a plurality of ring structures joined by first and second sets of connector segments, each of the first set of connector segments joining only an adjacent pair of the plurality of ring structures and each of the second set of connector segments joining at least three ring structures of the plurality of ring structures, the first axial portion including connector segments of both the first and second sets of connector segments and the second axial portion including connector segments of only the first set of connector segments; and
   a valve member attached to the support frame and forming a valve opening that opens to permit fluid flow through the support frame in a first direction and closes to substantially prevent fluid flow through the support frame in a second, opposite direction;
   wherein each of the proximal and distal ends of the support frame comprises only one ring structure of the plurality of ring structures; and
   wherein the first axial portion includes the proximal end of the support frame and the second axial portion includes the distal end of the support frame and at least two adjacent ring structures of the plurality of ring structures, one of which is directly joined to the ring structure of the distal end by a connector segment of the first set of connector segments.

2. A medical device according to claim 1, wherein each connector segment of the second set of connector segments is spaced from at least one connector segment of the first set of connector segments by at least one peak in the undulating pattern of a ring structure.

3. A medical device according to claim 1, wherein each connector segment of the second set of connector segments is spaced from at least one connector segment of the first set of connector segments by at least two peaks in the undulating pattern of a ring structure.

4. A medical device according to claim 1, wherein the second set of connector segments comprises first and second connector segments diametrically disposed on said support frame.

5. A medical device according to claim 1, wherein each connector segment of the second set of connector segments joins less than half of the ring structures of the plurality of ring structures.

6. A medical device according to claim 1, wherein each connector segment of the second set of connector segments joins less than one third of the ring structures of the plurality of ring structures.

7. A medical device according to claim 1, wherein the plurality of ring structures comprises first and second pairs of adjacent ring structures;
   wherein the first pair of adjacent ring structures is joined by a first number of connector segments of the first set of connector segments;
   wherein the second pair of adjacent ring structures is joined by a second number of connector segments of the first set of connector segments;
   wherein the first number is different than the second number.

8. A medical device according to claim 1, wherein the valve member comprises a bioremodellable material.

9. A medical device according to claim 1, wherein the valve member comprises an extracellular matrix material.

10. A medical device according to claim 1, wherein the valve member comprises small intestine submucosa.

11. A medical device according to claim 1, wherein the valve member comprises a tubular member attached to the support frame.

12. A medical device according to claim 1, wherein the valve member comprises a tissue valve.

13. A medical device according to claim 12, wherein the tissue valve comprises a heart valve.

14. A medical device according to claim 1, wherein the valve member is attached to the support frame at the first axial portion.

* * * * *

UNITED STATES PATENT AND TRADEMARK OFFICE
CERTIFICATE OF CORRECTION

| | | |
|---|---|---|
| PATENT NO. | : 7,544,205 B2 | Page 1 of 1 |
| APPLICATION NO. | : 11/314661 | |
| DATED | : June 9, 2009 | |
| INVENTOR(S) | : Jacob Flagle and Brian C. Case | |

It is certified that error appears in the above-identified patent and that said Letters Patent is hereby corrected as shown below:

Title Page, item [75], inventor's name "Brain C. Case" should read --Brian C. Case--.

Signed and Sealed this

Fourteenth Day of July, 2009

JOHN DOLL
*Acting Director of the United States Patent and Trademark Office*